(12) United States Patent
Hamboly

(10) Patent No.: US 9,919,143 B2
(45) Date of Patent: Mar. 20, 2018

(54) MEDICAL CONNECTION DEVICE WITH VALVE AND METHOD

(71) Applicant: M. Samy Ahmed Hamboly, 10th of Ramadan (EG)

(72) Inventor: M. Samy Ahmed Hamboly, 10th of Ramadan (EG)

(73) Assignee: Catheter IP Holding Company Ltd., Limassol (CY)

(*) Notice: Subject to any disclaimer, the term of this patent is extended or adjusted under 35 U.S.C. 154(b) by 589 days.

(21) Appl. No.: 14/048,667

(22) Filed: Oct. 8, 2013

(65) Prior Publication Data

US 2014/0107618 A1   Apr. 17, 2014

Related U.S. Application Data

(60) Provisional application No. 61/713,242, filed on Oct. 12, 2012.

(51) Int. Cl.
*A61M 31/00* (2006.01)
*A61M 39/24* (2006.01)

(52) U.S. Cl.
CPC ....... *A61M 39/24* (2013.01); *A61M 2039/244* (2013.01); *A61M 2039/2426* (2013.01)

(58) Field of Classification Search
CPC .......... A61M 39/24; A61M 2039/2426; A61M 2039/244; A61M 2039/2433; A61M 2039/027; A61M 2039/064; A61M 2039/246; A61M 2039/261–2039/263; A61M 2039/062; A61M 2039/0626; A61M 2039/0633; A61M 2039/0673; A61M 2039/0686; A61M 39/06; A61M 39/26; A61M 39/0606; A61M 39/0693; F16L 37/38
USPC .......................................................... 604/513
See application file for complete search history.

(56) References Cited

U.S. PATENT DOCUMENTS

| | | | | |
|---|---|---|---|---|
| 4,917,668 | A * | 4/1990 | Haindl | A61M 39/26 604/167.03 |
| 5,176,652 | A * | 1/1993 | Littrell | A61M 39/0606 137/849 |
| 6,171,287 | B1 * | 1/2001 | Lynn | A61M 39/02 251/149 |
| 6,428,520 | B1 * | 8/2002 | Lopez | A61M 39/045 251/149.3 |
| 6,551,283 | B1 * | 4/2003 | Guo | A61M 39/06 251/149.1 |
| 8,211,089 | B2 | 7/2012 | Winsor et al. | |

(Continued)

*Primary Examiner* — Kevin C Sirmons
*Assistant Examiner* — Leah Swanson
(74) *Attorney, Agent, or Firm* — Decker, Jones P.C.; Brian K. Yost; Geoffrey A. Mantooth

(57) ABSTRACT

The assembly is generally tubular and comprises a female connector portion comprising a cannula adapted to receive a male connector, the female connector portion comprising one or more septum units. Each of the septum units comprises slits and flaps. The flaps, when in a closed position, substantially close the cannula. The septum units are positioned adjacent to one another in a "back to back" orientation such that the first septum slits are transverse to the corresponding second septum slits such that the slits of the first septum are supported by flaps of the second septum and slits of the second septum are supported by flaps of the first septum.

16 Claims, 2 Drawing Sheets

(56) References Cited

U.S. PATENT DOCUMENTS

2008/0132833 A1* 6/2008 Harding ............... A61M 25/00
                                                604/93.01
2012/0130319 A1   5/2012 Moorehead et al.

* cited by examiner

MEDICAL CONNECTION DEVICE WITH VALVE AND METHOD

This application claims the benefit of U.S. provisional application Ser. No. 61/713,242, filed Oct. 12, 2012.

FIELD OF THE INVENTION

The present invention relates generally to a connection device for connecting medical devices and specifically to a medical connection device comprising an improved valve assembly, and a method for preventing reflux and air ingestion.

BACKGROUND OF THE INVENTION

In the medical field, it is often necessary to attach instruments and tubes to one another. For example, catheters, syringes, needles and IV tubes must often be connected to one another, so that, for example, hemodialysis and other infusion procedures may be safely performed. Various connection systems permitting attachments of such medical devices are commercially available. For example, many medical devices are manufactured with luer slip or luer lock connectors which are commonplace and used extensively in health care facilities throughout the world. Today, luer connectors are commonly used to connect a variety of vascular, enteral, respiratory, and epidural medical devices, components, and accessories. The International Organization for Standardization (ISO) provides that a luer connector has a "conical fitting with a 6% taper for syringes, needles, and certain other medical equipment." ISO 594-1:1986. Therefore, these connectors generally comprise round male and female interlocking tubes which are slightly tapered so as to hold together upon gentle insertion. A luer slip connection is made by a friction fitting between the male and female tubes. A luer lock connection comprises an additional outer rim of threading which permits the male and female tubes to be secured or "locked" into position. Luer slip connections are often used to connect the intravenous infusion supply tube to the hub of a cannula placed within a patient's vein. Luer lock connections may be used in similar applications, but especially in those in which it is desired to have a more secure connection between devices. Because luer connections offer near universal fit and compatibility, such connections have become ubiquitous. However, as it is desirable to prevent "misconnections" or connections in which two unrelated delivery systems are mistakenly connected together, in recent years alternative connectors have been developed and brought to the marketplace. Regardless of the connection used for a particular system, the connectors form the same general function of permitting different components to be linked together.

One of the known issues associated with luer and other vascular connection devices is the danger of reflux of blood or other fluids into the infusion apparatus. With blood reflux, small amounts of blood from the patient may be drawn into the infusion apparatus, sometimes resulting in blood clots or blockages within the apparatus and other undesirable complications. Another known issue associated with intravenous catheter connections relates to air ingestion through the catheter into the patient's blood stream. This may occur, for example, when the infusion tube is disconnected from an in-vein catheter, leaving the distal connection/female luer end (the end farthest from the patient) exposed to room air.

DESCRIPTION OF THE PRIOR ART

Various efforts have been made to prevent reflux of blood into the infusion apparatus and to prevent air ingestion through the catheter into the patient's blood stream. In prior art infusion systems, for example, clamps are often attached to both the infusion device (catheter for example) and the infusion line before connecting the female luer to male luer. After making such connections, the clamps are then opened. Likewise, before disconnection of such prior art connections, the clamps are re-closed in order to prevent reflux and/or air ingestion.

Others have developed improved connectors to alleviate blood reflux and air ingestion. For example, Winsor et al. U.S. Pat. No. 8,211,089 provides a device comprising a split septum and pressure activated flow control valve. Moorehead et al., US Patent Publication 2012/0130319, provides a valved catheter comprising a pressure active two-way slit valve assembly. However, the Winsor device is relatively complicated and provides for two separate assemblies of wholly different construction. The Moorehead device comprises a simplistic assembly comprising an irregular conduit.

There is, accordingly, a need for a connection device comprising an improved valve assembly. In the female luer with valve system provided herein, there is no need for the clamps, as the valve is self-sealing and will prevent blood reflux or air ingestion.

BRIEF DESCRIPTION OF THE DRAWINGS

FIG. 1 B is a cross sectional view of the assembly illustrating the septa flaps protruding with advancement of the male luer slip, in accordance with a preferred embodiment.

FIG. 1 C is a cross sectional view of the assembly illustrating the septa flaps returning to position when the male luer slip is withdrawn.

FIG. 2 B is a cross sectional view of the assembly illustrating the septa flaps protrusion and cone compression with advancement of the male luer slip.

FIG. 2 C is a cross sectional view of the assembly illustrating the septa flaps returning to position and releasing the compressed cone when the slip luer is withdrawn.

FIG. 3 B is an upper view of the luer connector showing the crossing of the slit cuts.

DESCRIPTION OF THE PREFERRED EMBODIMENT

Referring to FIGS. 1A-3B, improved connector assemblies for infusion of fluids are shown. As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment," "certain embodiments," "an embodiment," or similar term means that a particular feature, structure, or characteristic described in connection with the embodiment is included in at least one embodiment of the present disclosure. Thus, the appearances of such phrases in various places throughout this specification are not necessarily all referring to the same embodiment. Furthermore, the particular features, structures, or characteristics may be combined in any suitable manner on one or more embodiments without limitation. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

The examples and illustrations of a connection system for a catheter are described herein with respect to connection of a single lumen or dual lumen catheter to an infusion assembly. However, the inventive connection system is equally applicable for use with other catheters. Moreover, while certain materials are discussed herein with respect to the components of a catheter, connection system, adaptor, etc., the connection system is not limited to such materials. The terms "proximal" and "distal" shall mean, unless the connotation suggests otherwise, a position closer and further from/to the patient, respectively.

In the preferred embodiment of the medical connection device, a luer connection between a catheter shaft and an infusion assembly is provided. The catheter shaft which may be coupled to the device may comprise polyurethane, silicone or like material (e.g., a soft plastic or elastomer). Although, the medical connection device of the preferred embodiment comprises a modified luer connector, the connector need not be a luer type connector. Rather, other connectors may be modified in accordance with this specification without departing from the scope and spirit of this disclosure. For example, in other embodiments, the connector may comprise barbs or ridges on an outer surface.

Figure 1A:
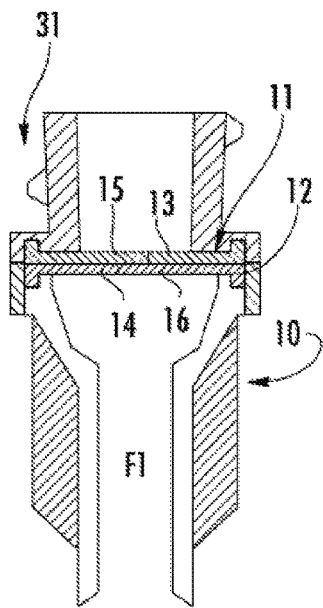
FIG. 1 A is a cross sectional view of the assembly showing the position of the two septum units, in accordance with a preferred embodiment.
Figure 1B:
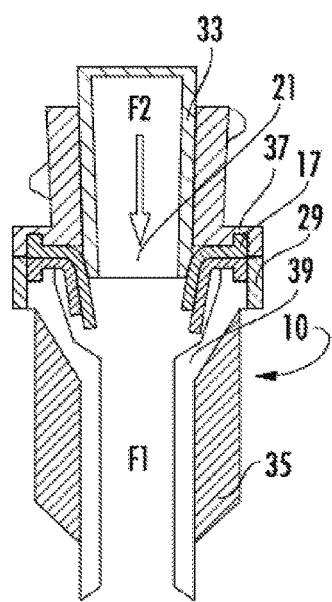
Figure 1C:
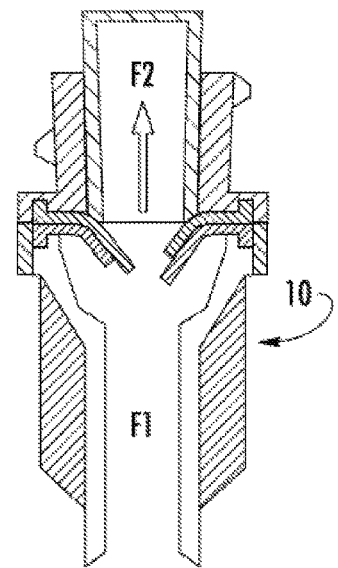
Figure 3A:
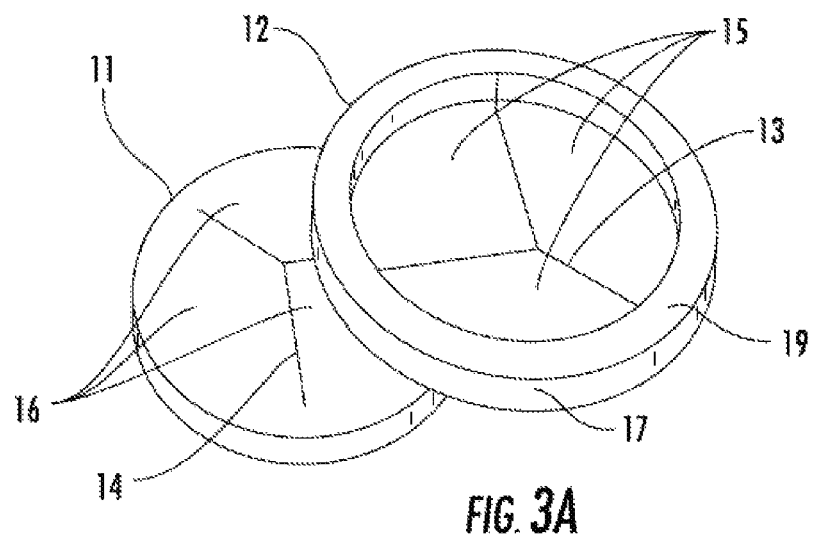
FIG. 3 A is an isometric view of the septum units with preferred slit cuts and flaps in accordance with a preferred embodiment.
Figure 3B:
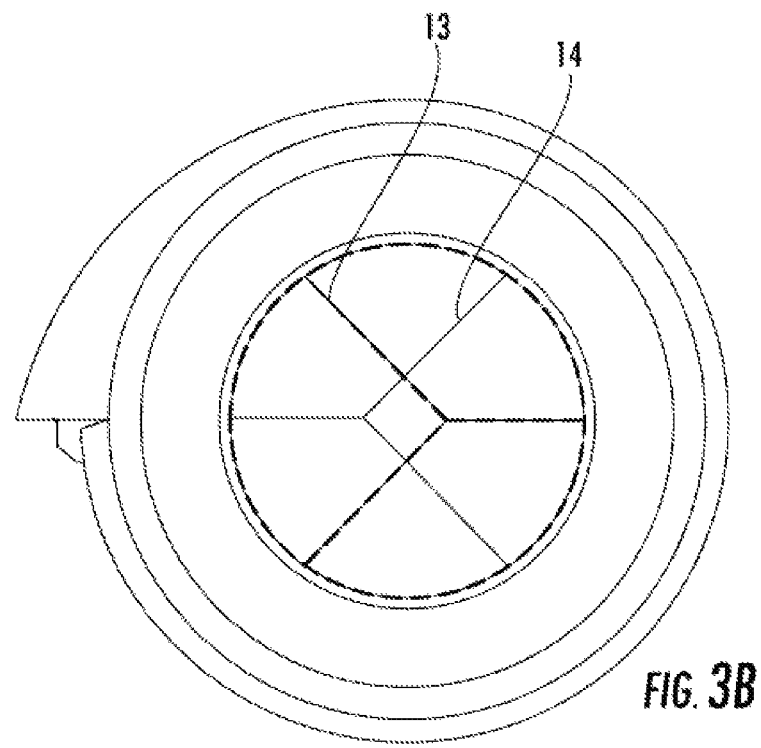

Referring to FIGS. 1 A-1 C & FIGS. 3 A and 3 B, an improved connector assembly for infusion of fluids is shown. The assembly 10 is generally tubular and comprises a female connector portion 31 adapted to receive a male connector 33, the female connector portion 31 comprising one or more septum units 11, 12. In the preferred embodiment, the assembly 10 comprises first and second generally identical septum units 11, 12 which prevent the reflux of blood from the female connector portion 31. The assembly 10 further comprises a barrel 29, outer wall 35, and inner wall 39. Confined within inner wall 39 is female fluid conduit F1. Barrel 29 comprises an outside diameter slightly larger than an outside diameter of the female connector portion 31 and an outside diameter of outer wall 35 such that a shoulder is formed. An interior portion of said barrel 29 comprises a seat 37 or indented portion 37 adapted to receive a corresponding ridge portion 19 of one or more of the septum units 11, 12. In the preferred embodiment, the assembly 10 comprises a modified luer connection.

Each of the septum units 11, 12 comprise slits 13, 14, flaps 15, 16, and a housing ring 17. The ring 17 is a truncated tubular member 17 to which the flaps 15, 16 are flat pieces formed from a flexible material having generally low water and vapor permeability properties. In the preferred embodiment, the flaps 15, 16 are formed from such material and are coupled to the ring 17 on a lower surface of the ring 17. The flaps 15, 16, when in a closed position as shown in FIGS. 3 A and 3 B, substantially close a lower ring opening 21.

In the preferred embodiment, each slit 13, 14 comprises a generally "Y" shaped configuration. The "Y" configuration is formed by three cuts radiating from an eccentric or slightly off center position. The two septum units 11, 12 are positioned adjacent to one another in a "back to back" orientation such that the first septum 11 slits 13 are transverse to the corresponding second septum 12 slits 14 such that the slits 13 of the first septum 11 are supported by flaps 16 of the second septum 12 and slits 14 of the second septum 12 are supported by flaps 15 of the first septum 11. This transverse orientation of the first and second septa slits 13, 14 strengthens the septum units 11, 12 against fluid communication or flux through slit cuts 13, 14.

The septa flaps 15, 16 protrude proximally upon insertion of the male luer slip 33 into the luer connector assembly 10 and hence open the septum units 11, 12 and the fluid pathway (F1) of the female male luer connector assembly 10 will be in continuation of the fluid pathway (F2) of the male luer assembly 33. In such orientation, the fluid can flow from either direction without any resistance. Upon removal of the slip of the male luer 33, the septa flaps 15, 16 return to their original position and prevent fluid communication or flow from the female luer assembly 31.

Figure 2A:
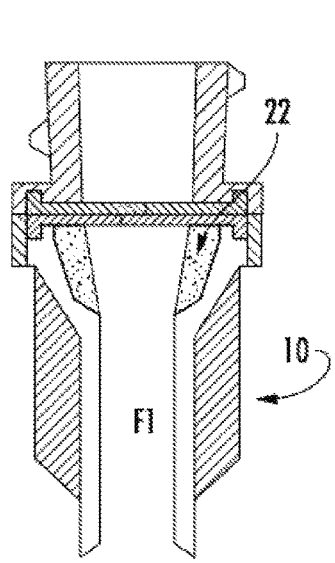
FIG. 2 A is a cross sectional view of the assembly showing the position of the two septum units and the soft cone, in accordance with another embodiment.
Figure 2B:
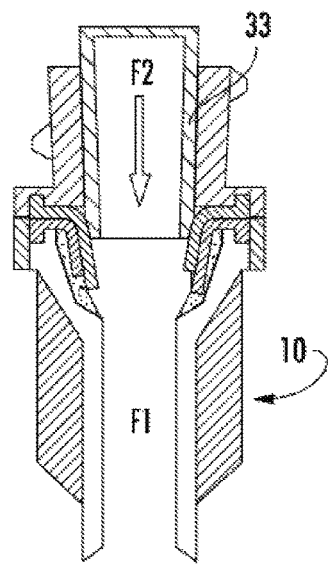
Figure 2C:
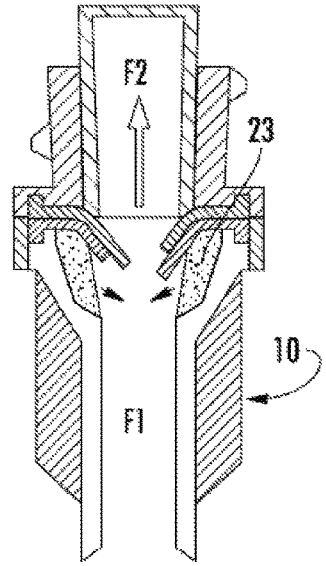

Referring to FIGS. 2 A-2 C, another embodiment of the improved connector assembly 10 for infusion of fluids is shown. The connector assembly 10 comprises a hollow, generally cone shaped portion 22 comprising a soft compressible material. In this embodiment, this material is preferably silicone. However, other soft compressible materials may be used without departing from the scope and spirit of the invention. The hollow cone 22 is positioned within the connector assembly 33 just below the septum units 11, 12 so as when the septum units flaps 15, 16 are displaced by the advancement of the male luer slip 33, the flaps 15, 16 will compress the soft cone 22. When the male slip 33 is withdrawn, the flaps 15, 16 return to their position, releasing the compression on the soft cone 22. Release of the soft cone 22 generates an inner pressure 23 that pushes fluids out of the luer connector assembly 10 fluid pathway (F2).

The present invention also provides a method of preventing fluid reflux from a fluid catheter connection assembly 10. The method comprises the steps of providing a connector assembly 10 for infusion of fluids, the assembly 10 comprising a female connector portion 31 adapted to receive a male connector 33, the female connector portion 31 comprising first and second identical septum units 11, 12; and coupling an end of said assembly 10 to a catheter tube.

In one embodiment of the method of preventing fluid reflux from a fluid catheter connection assembly 10, the assembly comprises a soft cone portion 22.

In one embodiment of the method of preventing fluid reflux from a fluid catheter connection assembly 10, one or more of the septum units 11, 12 comprise flaps 15, 16 comprising slits 13, 14. In another embodiment, the slits are "Y" shaped.

The present invention also provides a method of preventing air ingestion from a fluid catheter connection assembly 10. The method comprises the steps of providing a connector assembly 10 for infusion of fluids, the assembly 10 comprising a female connector portion 31 adapted to receive a male connector 33, the female connector portion 31 comprising first and second identical septum units 11, 12; and coupling an end of said assembly 10 to a catheter tube.

In one embodiment of the method of preventing air ingestion from a fluid catheter connection assembly 10, the assembly comprises a soft cone portion 22.

In one embodiment of the method of preventing air ingestion from a fluid catheter connection assembly 10, the soft cone portion 22 comprises silicone.

In one embodiment of the method of preventing air ingestion from a fluid catheter connection assembly 10, one or more of the septum units 11, 12 comprise flaps 15, 16 comprising slits 13, 14. In another embodiment, the slits are "Y" shape.

The present invention also provides a method of preventing fluid reflux and air ingestion through a fluid catheter connection assembly 10 comprising the steps of:

providing a connector assembly 10 for infusion of fluids, the assembly 10 comprising a female connector portion 31 comprising a cannula comprising a passage F1 therein;

said passage F1 comprising ends;

said female connector portion 31 comprising first 11 and second 12 septum units, each of said septum units 11, 12 comprising slits 13, 14;

said septum units 11, 12 occluding said passage F1 when in a first position and opening said passage when in a second position;

passing a male slip 33 into one end of said passage F1;

contacting the first septum unit 11 with an end of said male slip 33;

using said male slip 33, forcing said first septum unit 11 into the second septum unit 12 such that said first 11 and second 12 septum units are in the second position, thereby opening said passage F1; and retracting said male slip 33 from said passage F1 such that said first 11 and second 12 septum units return to said first position, thereby closing said passage.

In one embodiment of the method of preventing fluid reflux and air ingestion through a fluid catheter connection assembly 10, the assembly comprises a soft cone portion 22.

In one embodiment of the method of preventing fluid reflux and air ingestion through a fluid catheter connection assembly 10, the soft cone portion 22 comprises silicone.

In one embodiment of the method of preventing fluid reflux and air ingestion through a fluid catheter connection assembly 10, one or more of the septum units 11, 12 comprise flaps 15, 16 comprising slits 13, 14. In another embodiment, the slits are "Y" shape.

The foregoing disclosure and showings made in the drawing are merely illustrative of the principles of this invention and are not to be interpreted in a limiting sense. While the invention is shown in only a few forms, it is not just limited to the forms shown, but is susceptible to various changes and modifications without departing from the spirit thereof. The foregoing description of a preferred embodiment of the invention has been presented for the purpose of illustration and description. It is not intended to be exhaustive or to limit the invention to the precise form disclosed. Obvious modifications or variations are possible in light of the above teachings. The invention may be adapted for use in a number of environments.

The embodiment was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention in accordance with the breadth of this disclosure and the appended claims, to which it is fairly, legally, and equitably entitled to be interpreted.

I claim:

1. An improved connector assembly comprising:
a female connector portion comprising a cannula comprising a passage, the passage extending between first and second ends of the cannula;
a plurality of septum units;
said septum units being positioned within said cannula;
said cannula being adapted to receive a slip portion of a male connector;
said septum units each comprising slits defining flaps;
said flaps, when in a first position, occluding said passage, and when in a second position, opening said passage;
the cannula further comprising a cone shaped portion defined by a cone shaped perimeter wall comprising resilient material, the cone shaped perimeter wall defining a distally tapering space;
said space being unobstructed by the septum units when the flaps are in the first position; and
said cone shaped perimeter wall surrounding the passage of the cannula and being positioned between the flaps and the cannula second end when the flaps are in the first position such that the flaps, when in the second position, come in contact with and compress the cone shaped portion.

2. The improved connector assembly of claim 1, wherein:
the female connector portion comprising a shoulder defining a seat, each of said septum units comprising a housing ring, said rings being positioned within said seat.

3. The improved connector assembly of claim 1, wherein:
said plurality of septum units comprising first and second septum units, said flaps of said first septum unit overlapping said slits of said second septum unit when the flaps of the first and second septum units are in the first position.

4. The improved connector assembly of claim 1, wherein:
said plurality of septum units comprising first and second septum units sharing a central longitudinal axis;
when the flaps of the first septum unit are in the first position, said slits of said first septum unit extending from a first septum unit outer perimeter and converging at a first septum off-center position with respect to said central longitudinal axis;
when the flaps of the second septum unit are in the first position, said slits of said second septum unit extending from a second septum unit outer perimeter and converging at a second septum off-center position with respect to said central longitudinal axis; and
the first and second septum units being arranged such that the off-center position of the first septum unit is different from the off-center position of the second septum unit.

5. The improved connector assembly of claim 1, wherein:
said septum units being arranged adjacent to one another.

6. The improved connector assembly of claim 5, wherein said slits of each septum unit do not align with the slits of an adjacent septum unit.

7. The improved connector assembly of claim 6, wherein:
said slits of at least one of said septum units comprising a "Y" configuration.

8. An improved connector assembly comprising:
a female connector portion comprising a cannula and first and second septum units;
said cannula comprising a passage, the passage extending between first and second ends of the cannula;
a male connector comprising a slip portion;
said septum units being positioned within said cannula;

said cannula being adapted to receive the slip portion of said male connector;

said septum units each comprising slits defining flaps;

said flaps, when in a first position, occluding said passage, and when in a second position, opening said passage;

the female connector portion further comprising a shoulder defining a seat, each of said septum units comprising a housing ring, said rings being positioned within said seat;

said flaps of said first septum unit overlapping said slits of said second septum unit, when the flaps of the first and second septum units are in the first position;

the cannula further comprising a cone shaped portion defined by a cone shaped perimeter wall comprising resilient material, the perimeter wall defining a distally tapering space;

the cone shaped portion being positioned between the flaps and the cannula second end when the flaps are in the first position;

said space being unobstructed by the first and second septum units when the flaps are in the first position; and said cone shaped portion being adapted to be contacted and compressed by said flaps when said slip portion is in an inserted position.

9. The improved connector assembly of claim 8, wherein said septum units are arranged adjacent to one another.

10. The improved connector assembly of claim 8, wherein said slits of at least one of said septum units comprise a "Y" configuration.

11. A method of preventing fluid reflux and air ingestion through a fluid catheter connection assembly comprising the steps of:

providing a connector assembly for infusion of fluids, the assembly comprising a female connector portion comprising a cannula comprising a passage therein, the passage extending between first and second ends of the cannula;

said passage comprising first and second passage ends;

said female connector portion comprising first and second septum units, each of said septum units comprising slits;

said septum units occluding said passage when in a first position and opening said passage when in a second position;

the cannula further comprising a cone shaped portion defined by a cone shaped perimeter wall comprising resilient material, the perimeter wall defining a distally tapering space;

said space being unobstructed by the septum units when the septum units are in the first position;

said cone shaped portion being positioned between the septum units and the cannula second end when the septum units are in the first position;

the cone shaped portion being adapted to be contacted and compressed by the septum units when the septum units are in the second position;

passing a male slip into the passage first end;

contacting the first septum unit with an end of said male slip;

using said male slip, forcing said first septum unit into the second septum unit such that said first and second septum units are in the second position, thereby opening said passage; and retracting said male slip from said passage such that said first and second septum units return to said first position, thereby closing said passage.

12. The method of preventing fluid reflux and air ingestion through a fluid catheter connection assembly of claim 11, wherein:

said first and second septum units comprise flaps, said flaps of said first septum unit overlapping said slits of said second septum unit when the first and second septum units are in the first position.

13. The method of preventing fluid reflux and air ingestion through a fluid catheter connection assembly of claim 12, wherein:

said first and second septum units share a central longitudinal axis;

when the flaps of the first septum unit are in the first position, said slits of said first septum unit extend from a first septum unit outer perimeter and converge at a first septum off-center position with respect to said central longitudinal axis;

when the flaps of the second septum unit are in the first position, said slits of said second septum unit extend from a second septum unit outer perimeter and converge at a second septum off-center position with respect to said central longitudinal axis; and the first and second septum units being arranged such that the off-center position of the first septum unit is different from the off-center position of the second septum unit.

14. The method of preventing fluid reflux and air ingestion through a fluid catheter connection assembly of claim 13, wherein:

said slits of at least one of said septum units comprise a "Y" configuration.

15. The method of preventing fluid reflux and air ingestion through a fluid catheter connection assembly of claim 11, wherein:

the female connector portion comprises a shoulder defining a seat, each of said septum units comprising a housing ring, said rings being positioned within said seat.

16. The method of preventing fluid reflux and air ingestion through a fluid catheter connection assembly of claim 11, wherein:

said septum units are arranged adjacent to one another.

* * * * *